United States Patent [19]
Vives

[11] 3,960,921
[45] June 1, 1976

[54] DIHALODICYANO ALKENES
[75] Inventor: Van C. Vives, Bartlesville, Okla.
[73] Assignee: Phillips Petroleum Company, Bartlesville, Okla.
[22] Filed: Apr. 14, 1975
[21] Appl. No.: 567,828

Related U.S. Application Data
[63] Continuation-in-part of Ser. No. 451,474, March 15, 1974, abandoned.

[52] U.S. Cl. ............... 260/464; 204/158 HA; 260/465 G; 260/465.7
[51] Int. Cl.$^2$ ............ C07C 121/30; C07C 121/48; C07C 121/70
[58] Field of Search ............ 260/465.7, 465 G, 464; 204/158 AA, 158 HA

[56] References Cited
UNITED STATES PATENTS

| | | | |
|---|---|---|---|
| 3,057,875 | 10/1962 | Brown | 260/465.7 X |
| 3,079,421 | 2/1963 | Martin | 260/465.7 X |
| 3,133,115 | 5/1964 | Proskow | 260/465.7 |
| 3,238,228 | 3/1966 | Linn | 260/465.7 X |
| 3,637,800 | 1/1972 | Burton et al. | 260/465.7 |

OTHER PUBLICATIONS
Beech, et al., C.A., 50, (1956), 813.
Schlogl, et al., C.A., 55, (1961), 22227–22228.
Hatten, et al., C.A., 69, (1968), 95924.
Heasley et al., C.A., 71, (1969), 90705.

*Primary Examiner*—Joseph P. Brust

[57] ABSTRACT

Described herein are novel dihalodicyano alkene compounds having the formula $$X-\underset{R'}{\overset{R}{C}}-\underset{}{\overset{CN}{C}}=\underset{}{\overset{CN}{C}}-\underset{R'}{\overset{R}{C}}-X$$

having from 6 to 38 carbon atoms per molecule, wherein X is chloro or bromo; each R is individually selected from the group consisting of hydrogen, alkyl, cycloalkyl and aryl; and each R' is individually selected from the group consisting of hydrogen, alkyl and cycloalkyl.

5 Claims, No Drawings

DIHALODICYANO ALKENES

This application is a continuation-in-part of application Ser. No. 451,474, filed Mar. 15, 1974, now abandoned.

This invention relates to novel dihalodicyano alkene compounds.

It is an object of this invention to prepare certain novel compounds.

It is another object to provide a novel process for the preparation of dihalodicyano alkenes.

Other objects of this invention will be apparent from the detailed description which follows.

The novel compounds of the present invention have the following general formula

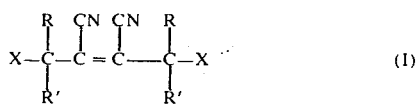

and contain from 6 to 38 carbon atoms per molecule, wherein X is a halogen selected from the group consisting of chlorine and bromine; each R is individually selected from the group consisting of hydrogen, alkyl having from 1 to 4 carbon atoms, cycloaklyl having from 3 to 6 carbon atoms, aryl having from 6 to 10 carbon atoms, and combinations thereof; and each R' is individually selected from the group consisting of hydrogen, alkyl having from 1 to 4 carbon atoms, cycloaklyl having from 3 to 6 carbon atoms, and combinations thereof.

In a presently preferred embodiment, when R or R' is a cycloaklyl or tertiary alkyl group, no more than one such R or R' group is attached to a single carbon atom.

In a more preferred embodiment, the above-described compound has no more than one cycloaklyl, tertiary alkyl or aryl group per molecule.

The novel compositions of matter 1,4-dibromo-,2,3-dicyano-2-butene and 1,4-dichloro-2,3-dicyano-2-butene are prepared, respectively, by the 1,4-addition of bromine or chlorine to 1,3-butadiene-2,3-dicarbonitrile. The addition of halogen to the conjugated diene is promoted by the use of ultraviolet light irradiation but the addition can also be carried out in the presence of a small amount of hydrogen halide in diffuse daylight.

In general, the compounds of this invention are prepared by reacting chlorine or bromine with the corresponding dicyano-substituted conjugated diene according to the following general reaction equation:

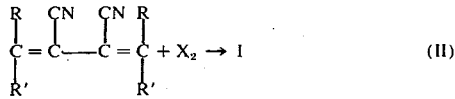

wherein X, R and R' are as defined above. The process of this invention generally provides a mixture of isomers such as cis/trans isomers. A single generic structural formula (I) of the novel compounds is shown for convenience. Although formula (I) suggests the cis isomeric configuration, it should be understood that the present invention process can produce both cis and trans isomers and, most frequently, a mixture of these.

The above reaction is preferably carried out in the presence of a halogenation promoter which can be ultraviolet irradiation or a small amount of hydrogen halide such as hydrogen iodide, hydrogen bromide or hydrogen chloride, or any combination thereof. It is presently preferred that the above reaction be carried out utilizing ultraviolet irradiation.

Representative compounds described by formula II include the following: 1,3-butadiene-2,3-dicarbonitrile; 2,4-hexadiene-3,4-dicarbonitrile; 1,3-pentadiene-2,3-dicarbonitrile; 5,7-dodecadiene-6,7-dicarbonitrile; 1-phenyl-1,3-butadiene-2,3-dicarbonitrile; 1-p-tolyl-1,3-butadiene-2,3-dicarbonitrile; 5,8-di-n-butyl-5,7-dodecadiene-6,7-dicarbonitrile; 2,9-dimethyl-4,7-diphenyl-4,6-decadiene-5,6-dicarbonitrile; 1-cyclopropyl-1,3-butadiene-2,3-dicarbonitrile; 1-cyclohexyl-1,3-butadiene-2,3-dicarbonitrile; 1-alphanapthyl-1,3-butadiene-2,3-dicarbonitrile; 2,4-octadiene-3,4-dicarbonitrile, and the like.

In a presently preferred embodiment, the dicyano-substituted conjugated diene of formula II is 1,3-butadiene-2,3-dicarbonitrile, which, on bromination or chlorination, gives 1,4-dibromo-2,3-dicyano-2-butene or 1,4-dichloro-2,3-dicyano-2-butene, respectively.

1,3-Butadiene-2,3-dicarbonitriles can be obtained by the known thermal isomerization of a cyclobutene-1,2-dicarbonitrile, which is prepared from a cyclobutane-1,2-dicarbonitrile, the thermal dimer of acrylonitrile or a substituted acrylonitrile.

The above reaction to prepare the compounds of formula (I) is conveniently carried out in any inert polar or non-polar solvent in which the reactants are soluble, as for example, chloroform, carbon tetrachloride, dichloromethane, chlorobenzene, etc.

The proportions of the reactants can be varied. Normally, a slightly greater than stoichiometric amount of halogen is used since this results in the most economical utilization of reactants. Thus, a molar ratio of halogen to diene in the range of 1:1 to 2:1 can be used. Higher ratios are to be avoided since production of undesirable side products can result. It is presently preferred that the molar ratio of halogen to diene be about 1.2:1.

Reaction time is dependent, inter alia, upon the reactants, halogenation promoter, temperature and the like. Reaction time is generally within the range of 0.1 to 24 hours.

The reaction temperature should normally be sufficiently high so that the reactants will dissolve to a substantial degree in the reaction medium, yet should be below the decomposition temperature of the reactants. Normally, the reaction is carried out at a temperature between about −50° and about 150°C. It is presently preferred that the reaction temperature be in the approximate range of 10° to 50°C.

The reaction is normally conducted under atmospheric pressure, although a pressure in the range of subatmospheric to superatmospheric can be used, preferably 0–100 psig.

The novel compounds of this invention can be isolated in conventional manner, such as by filtration, extraction, distillation and the like.

The compounds of this invention are useful as bactericides and herbicides. Application of the compounds of this invention for the purposes disclosed may be made from solutions in suitable solvent carriers, or in combination with supplementary agents, adjuvants, other control agents and the like. They are employed in a bactericidal or herbicidal effective amount, generally from about 0.01 to about 90 weight percent of the total composition.

The compounds of this invention are also useful as intermediates in the preparation of amides, carboxylic acids and amines.

The following examples illustrate the invention:

EXAMPLE I

A solution of 2.303 g (0.022 mol) of 1,3-butadiene-2,3-dicarbonitrile in 150 ml of chloroform was charged to a three-neck round-bottom flask cooled in an ice bath. The flask was fitted with a thermometer, dry ice cold finger condenser, dropping funnel and magnetic stirrer. A solution of 8.1 g (0.05 mol) of bromine in 100 ml of chloroform was added, dropwise, to the contents of the flask. Approximately 29 ml of the bromine solution was added over a 24 minute period. The flask containing the reaction mixture was then removed from the ice bath and allowed to warm to room temperature. A small amount of HBr was added to the reaction mixture. The remainder of the bromine solution was added over a period of 58 minutes.

After standing at room temperature overnight, the solution was concentrated under vacuum to give 7.14 g of residue. This residue was dissolved in ether and the ethereal solution was diluted with hexane and cooled to −20°C to induce crystallization. The crystals that formed were contaminated with an orange oil. Treatment of this material with activated charcoal in chloroform solution and recrystallization from hexane solution gave 3.54 g of light yellow crystals.

Elemental analysis:

Calc'd for $C_6H_4Br_2N_2$: C — 27.3%; H — 1.5%; Br — 60.6%; N — 10.6%.

Found: C — 27.4%; H — 1.6%; Br — 60.3%, N — 10.2%.

Nuclear magnetic resonance (nmr) and infrared (IR) spectral analyses, together with the elemental analysis, indicated that the light yellow crystalline product was 1,4-dibromo-2,3-dicyano-2-butene ($C_6H_4Br_2N_2$).

EXAMPLE II

A solution of 10 g (0.096 mol) of 1,3-butadiene-2,3-dicarbonitrile in 100 ml of chloroform was placed in a 3-neck round-bottom flask equipped with a cold water condenser, thermometer, dropping funnel and magnetic stirring device. A 40 ml solution of 17 g (0.106 mol) of bromine in chloroform was added, dropwise, to the contents of the flask over a 30 minute period, during which time the reaction mixture was irradiated with ultraviolet light and maintained at a temperature of 20°C. After all the bromine solution had been added, the reaction mixture was stirred without cooling for 1.5 hours; the temperature of the reaction mixture gradually increased to 35°C and its color changed from red to light orange.

The reaction mixture was concentrated under vacuum to give an orange colored oily residue. The residue was dissolved in dichloromethane, treated with activated charcoal and filtered, giving a dark orange filtrate. The filtrate was concentrated then cooled to −20°C, to induce crystallization. The resulting crystals were again treated with activated charcoal in dichloromethane. Three additional recrystallizations from dichloromethane-hexane gave 12.4 g of yellow crystals which melted to a colorless oil at 106°–112°C.

Elemental analysis:

Calc'd for $C_6H_4Br_2N_2$: C — 27.3%; H — 1.5%; Br — 60.6%; N — 10.6%.

Found: C — 27.3%; H — 1.5%; Br — 58.9%; N — 10.7%.

The product, 1,4-dibromo-2,3-dicyano-2butene, is believed to be a mixture of cis and trans isomers.

EXAMPLE III

Samples of the 1,4-dibromo-2,3-dicyano-2-butene product of Example II were tested for herbicidal and bactericidal activity according to the following procedures.

In the herbicidal testing, seedlings of broadleaves (pigweed, morning glory, and velvetleaf) and seedlings of grasses (red millet, foxtail and Japanese millet) were treated with a test formulation containing a dosage of 1,4-dibromo-2,3-dicyano-2-butene corresponding to 8 pounds per acre. After two weeks, 70% control was observed for the broadleaf seedlings; 85% control was observed for the grass seedlings.

In the bactericidal testing, 1,4-dibromo-2,3-dicyano-2-butene was incorporated into a nutrient medium to produce a concentration of 64 ppm (parts of 1,4-dibromo-2,3-dicyano-2-butene per million parts of medium, by weight). Three individual culture plates were inoculated, respectively, with *Escherichia coli*, *Haemophilus gallinarum* and *Staphylococcus aureus* bacteria and incubated for 48 hours. Growth of the organisms was inhibited by the presence of the 1,4-dibromo-2,3-dicyano-2-butene ("50% control," as evidenced by sparse growth and separated colonies).

This example demonstrates the effectiveness of 1,4-dibromo-2,3-dicyano-2-butene both as a herbicide and as a bactericide.

EXAMPLE IV

A solution of 4.6 g (0.044 mol) of 1,3-butadiene-2,3-dicarbonitrile in 100 ml of chloroform was placed in a three-neck round-bottom flask equipped with a thermometer, dry ice cold finger condenser, fritted glass bubbler for the introduction of chlorine gas and magnetic stirrer. Chlorine was passed through the reaction mixture over a period of about 3 hours while the reaction mixture was irradiated with ultraviolet light. During this period the temperature of the reaction mixture ranged from 22° to 38°C. Chlorine passage was stopped and the ultraviolet light source was removed. The reaction mixture was allowed to stand overnight at room temperature under a nitrogen atmosphere.

The product was isolated from the filtered reaction mixture by crystallization from a hexane solution. IR and nmr confirmed that the resulting white solid was 1,4-dichloro-2,3-dicyano-2-butene. Yield: 6.4 g.

It will be evident to those skilled in the art that various modifications of this invention can be made, or followed, in the light of the foregoing disclosure and discussion, without departing from the spirit or scope thereof.

I claim:

1. An isomirsic mixture of a dihalodicyano alkene of the formula

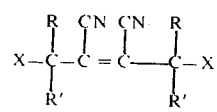

having from 6 to 38 carbon atoms per molecule, wherein X is a halogen selected from the group consisting of chlorine and bromine; each R is individually selected from the group consisting of hydrogen, alkyl having from 1 to 4 carbon atoms, cycloalkyl having from 3 to 6 carbon atoms and aryl having from 6 to 10 carbon atoms; and each R' is individually selected from the group consisting of hydrogen, alkyl having from 1 to 4 carbon atoms and cycloalkyl having from 3 to 6 carbon atoms.

2. The compound of claim 1 wherein X is chlorine, R is hydrogen and each R' is hydrogen.

3. The compound of claim 1 wherein X is bromine, R is hydrogen and R' is hydrogen.

4. The compound of claim 1 wherein when R or R' is a cycloalkyl or tertiary alkyl group, no more than one such group is attached to a single carbon atom.

5. The compound of claim 1 wherein only one of said R or R' is tertiary alkyl, cycloalkyl or aryl.

* * * * *